United States Patent [19]

Polaschegg

[11] Patent Number: 4,844,871

[45] Date of Patent: Jul. 4, 1989

[54] METHOD OF DETERMINING THE PARTIAL PRESSURE OF GASES IN BLOOD AND AN APPARATUS FOR PERFORMING THE METHOD

[75] Inventor: Hans-Dietrich Polaschegg, Oberursel, Fed. Rep. of Germany

[73] Assignee: Fresenius AG, Bad Homburg, Fed. Rep. of Germany

[21] Appl. No.: 47,648

[22] Filed: May 8, 1987

[30] Foreign Application Priority Data

May 13, 1986 [DE] Fed. Rep. of Germany ....... 3616062

[51] Int. Cl.⁴ .................... G01N 1/28; G01N 33/50
[52] U.S. Cl. ........................ 422/81; 128/632; 210/195.2; 210/321.6; 210/651; 422/44; 422/68; 436/43; 436/52; 436/68; 436/74; 436/150; 436/163; 436/178; 604/6
[58] Field of Search ............ 436/43, 52, 53, 74, 436/68, 150, 163, 177, 178; 422/44, 45, 68, 81, 82; 210/195.2, 321.6, 651; 128/632, 635; 604/6

[56] References Cited

U.S. PATENT DOCUMENTS

| | | | |
|---|---|---|---|
| 3,556,950 | 1/1971 | Dahms | 436/68 X |
| 3,634,039 | 1/1972 | Brondy | 422/81 X |
| 3,848,580 | 11/1974 | Hyden et al. | |
| 3,880,592 | 4/1975 | Kelley et al. | 436/177 X |
| 3,884,640 | 5/1975 | Lock et al. | 436/68 X |
| 4,191,182 | 3/1980 | Popovich et al. | 210/651 X |
| 4,640,820 | 2/1987 | Cooper | 436/68 X |
| 4,708,714 | 11/1987 | Larsson et al. | 604/6 X |
| 4,717,548 | 1/1988 | Lee | 422/68 |

FOREIGN PATENT DOCUMENTS

| | | |
|---|---|---|
| 3416956 | 12/1986 | Fed. Rep. of Germany . |
| 3524824 | 1/1987 | Fed. Rep. of Germany . |
| 79/01121 | 12/1979 | PCT Int'l Appl. ............ 210/195.2 |
| 2001755 | 2/1979 | United Kingdom . |

OTHER PUBLICATIONS

"Trends in Critical Care and Sensor Technology", Biomedical Business International, vol. VIII, No. 23/24, p. 232, 12/12/85.

Von Oswald Mueller-Plathe, *Sacure-Basen-Haushalt and Blutgase,* Second Edition, Klinische Chemie in Einzeldarstellangen, vol. 1, Georg Thieme-Verlag, Stuttgart, 1982, pp. 148 et seq.

*Primary Examiner*—Robert J. Hill, Jr.
*Attorney, Agent, or Firm*—Pravel, Gambrell, Hewitt, Kimball & Krieger

[57] ABSTRACT

A method and an apparatus are described for determining the partial pressures of gases in blood, in which a membrane filter is used to separate plasma which passes to a blood gas analyzer.

15 Claims, 2 Drawing Sheets

METHOD OF DETERMINING THE PARTIAL PRESSURE OF GASES IN BLOOD AND AN APPARATUS FOR PERFORMING THE METHOD

BACKGROUND OF THE INVENTION

The invention relates to the determination of the partial pressure of at least one gas in extracorporeally flowing blood in which the gas or gases are separated from the blood in a membrane filter and then brought into contact with at least one sensor responsive to such gas partial pressure.

The invention also relates to an apparatus for determining the partial pressures of gases in the blood comprising a filter, which is divided by a semipermeable membrane into two chambers, an extracorporeal blood conducting system conducted with one of the chambers and at least one sensor for measuring the partial pressure of the gas and which is connected by a duct with the other of the chambers of the filter.

Continuous monitoring of the acid-base parameters in the blood is particularly important during operations in which the patient is connected with a heart-lung machine and also during extracorporeal membrane oxygenation (ECMO). During such a procedure the partial pressures of oxygen and carbon dioxide are measured together with the pH value.

Furthermore, determination of these parameters upstream and downstream of the oxygenator is important for assessing the efficacy, or any drop in efficiency, of the oxygenator. Thus it is possible to distinguish between a change in the partial pressure of the blood due to a decrease in efficiency of the oxygenator and a change which is caused metabolically.

In order to obtain such data the normal course is to take occasional samples from the extracorporeal blood flow and then to analyze them in a blood gas analyzer. Such a procedure does however involve a substantial expense as regards staffing and equipment. For this reason sensors have been developed which are directly incorporated in the extracorporeal blood flow system and thus come into direct contact with the blood so that the blood gases may be continuously recorded in the extracorporeal blood flow system.

In connection with the use of such continuously operating sensors coming into direct contact with the blood, there is a calibration problem insofar as both the null point and also the slope of the response characteristic of such sensors may drift comparatively rapidly. It is more especially the case of cardiac operations lasting a matter of hours, or of ECMO lasting several days, that there is a serious problem here, since it is then not possible to obtain any reliable data.

Furthermore the direct connection of such sensors with an extracorporeal blood circuit tends to be problematical because there may be an interaction of the blood with the surface of the sensor and there is a risk of the sensitive surface of the sensor becoming clogged with a layer of blood components, that is to say the surface will be obscured by deposits and the data will be false.

In order to deal with this possibility procedures have been evolved in which the sensors were calibrated by the normal method prior to the treatment of the patient and samples were then taken at intervals during the treatment so that they might then be checked in a conventional blood gas analyzer. Apart from certain method errors and its complexity, this procedure did not make it possible to check or correct the slope of the response function of the sensor, because, for this to be done, two measurements at different partial pressure would be needed.

Moreover, in the case of such treatment making use of an extracorporeal circuit there is the necessity of measuring the concentrations of the blood electrolytes, something involving the taking of further samples.

An example in this respect is to be seen in an article in Biomedical Business International, Dec-12, 1985, Vol. VIII, No. 23/24, page 232 describing a device able to continuously measure not only blood gases but also electrolytes. For this purpose a continuously operating sampling device takes a small amount of the blood from the extracorporeal circuit or from the patient directly so that it may be continuously analyzed in the analyzer. This operation may be automatically interrupted at certain intervals, whereupon calibration solution is supplied to the device via valve means for renewed adjustment.

However it is a disadvantage in this respect that sampling is directly from the extracorporeal circuit or from the body of the patient since this will involve sterility problems. A further point is that entire blood is taken from the circuit which has to be conditioned with a sufficient amount of a clotting inhibitor so that the very act of adding such substance to the entire blood means that the gas equilibrium in the sample will be interfered with and the results of measurement falsified.

All in all, this previously proposed device involves an increased risk of contamination by the direct connection of the sampling device with the extracorporeal circuit.

It is furthermore stated in standard literature on the subject (see Oswald Mueller-Plathe: Saeure-Basen-Haushalt und Blutgase, second edition, Klinische Chemie by Einzeldarstellungen, Vol. 1, H. Breuer, H. Buettner, D. Stamm, published by Georg Thieme-Verlag, Stuttgart, 1982, page 148 et seq.) that the generally held opinion is that the determination of blood gases in plasma or serum leads to serious errors of measurement. In fact even a short time after the taking of a sample and separation of the red blood corpuscles, the oxygen partial pressure determined will be equal to the oxygen partial pressure in the atmosphere, because for separation of the erythrocytes and obtaining the plasma the entire blood is treated for some minutes in a centrifuge, the supernatant plasma then being drawn off with a syringe and being analyzed at once in a blood gas analyzer. However it has been found that even after a short centrifuging period the oxygen level will have risen by a factor of 2 to 3. Furthermore the carbon dioxide partial pressure will fall by approximately 20%, this corresponding to an increase in the pH value.

Accordingly the view has been taken so far that the determination of blood gases in plasma would not serve any useful purpose.

The German unexamined specification No. 2,725,757 describes a device of the initially mentioned type in which the blood is caused to pass through a dialysis filter, whose other side has a dialyzing liquid flowing through it. The substances to be determined diffuse through the pores of the membrane of the dialysis filter from the blood side to the dialyzing liquid side where they are conveyed with the dialyzing liquid to the analyzer. In order to make possible any form of quantitative determination it would be necessary for all method parameters to be kept constant, but this is not possible; for example the membrane becomes clogged with a secondary layer of proteins on the blood side and this increases the diffusion resistance by a factor of up to 5. A further varying parameter is the change in the electrolyte content of the blood from sample to sample even during the measuring period so that there are concentration gradients between the blood and dialysis liquid sides of the device. This also has a considerable interfering effect on the measuring operation.

A further point to be considered is that the blood and also the dialysis liquid have to be caused to pass through the dialysis filter at maximum velocity in order to avoid falsification in the concentration of the subtances to be determined. If, as is normally the case, peristaltic pumps are used, this will not be possible owing to pulsations which occur.

Since the diffusion of the substances to be determined is of paramount importance in the measuring operation, during calibration as well suitable calibrating solutions have to be supplied to the extracorporeal circuit, something which meets with intractable problems as regards cleaning and safefy. Furthermore the supply of such calibration solutions means that the protein layers deposited on the membrane surfaces will be removed again and this necessarily leads to a falsification of the measured data.

SHORT SUMMARY OF THE INVENTION

Accordingly one object of the present invention is to improve on the method of the type initially described in such a way that the gases in the blood may be quantitatively determined.

A further object of the invention is to provide an apparatus for this purpose.

Yet another object of the invention is to make it possible, in addition to quantitatively determining the blood gases, to simply calibrate the device without any problems and without interfering with the extracorporeal blood circuit.

In order to achieve these or other objects of the invention appearing herein, the plasma which comprises the gases to be determined, is separated from the rest of the blood by the membrane and while continuing to keep such plasma out of contact with air the partial pressure of at least one blood gas therein is determined.

For performing this method the invention also provides an apparatus in which the second chamber of the filter has a single outlet, which is connected with the duct designed to serve as the first plasma duct and a first plasma duct is connected with a unit for conveying plasma from the blood through the membrane of the membrane filter.

It has been surprisingly found that the plasma, which is separated with the aid of a membrane filter and is thereafter directly supplied to a blood gas analyzer, leads to a reproducible measurement data conforming to the blood data. Accordingly it is no longer necessary to interfere directly with the blood circuit using sampling devices so that the method of the invention is now free of the recognized risk of contamination. Membrane filters, which may be utilized in the extracorporeal circuit, normally have such a small pore size that they may be regarded as sterile filters, that is to say that the blood passed through the filter is not contaminated with microorganisms. The significant point with the method of the invention is that the plasma drawn off at the membrane filter is directly supplied to a sensor determining the gas partial pressure, something that is possible with the device of the invention.

Since the measurement is no longer dependent on diffusion but rather on the production of the ultrafiltrate in the form of the plasma filtrate, there is no necessity for calibration on the extracorporeal blood side. In fact, it is only important for the plasma produced at the membrane to completely fill the second chamber of the dialyzer and the plasma duct connected thereto so that there is no mixing thereof with the air, something which would otherwise lead to inaccurate data.

In a further development of the apparatus in accordance with the invention it is possible not only to determine the blood gases but also electrolyt4es and possibly further substances such as heparin in a continuous analytical procedure without involving any increased risk of contamination, since a plasma filter, selected in accordance with the purpose in hand, simultaneously acts as a sterile filter.

In accordance with a further embodiment of the invention, the method of the invention is only employed for determining blood gases. For this the use of a hemofilter is possible in the new method with which the filtrate is separated from the blood. Such hemofilters normally have a separation limit of approximately 40,000 to 60,000 atomic units of mass so that they do not only retain the blood corpuscles but also proteins with a high molecular weight, as for instance albumin and substances involved in blood clotting, on the blood side. Since these protein substances are partly electrically charged a concentration differential will arise between the blood and the filtrate in respect of the charged particles (ions), even if in view of their size the latter are able to freely pass through the membrane (Gibbs-Donnan effect). As a consequence of this the concentration of the ions may not be accurately determined using such a hemofilter.

Since however blood gases do not bear any electrical charge, they are not subject to this effect and are therefore able to be determined in the novel method using a hemofilter.

In keeping with a second embodiment of the invention the membrane filter may be in the form of a plasma filter with which plasma proteins may be separated and which normally has a separation limit of several millions of atomic units of mass. Since no charged blood components are retained at the filter, there is then no ion concentration differential between the blood and filtrate (plasma) so that a plasma produced in this manner may be examined both as regards the blood gas content and also as regards its content of ions. However a plasma obtained in this manner which contains all the proteins involved in clotting, and which for this reason is capable of clotting, must be treated with a substance inhibiting clotting such as heparin. If appropriate, it is thus possible for the plasma filtrate outlet to be connected with a device for administering such a substance preventing clotting, although this will not normally be required, since heparin is frequently added to the extracorporeal blood circuit and itself passes through the plasma filter like the other plasma proteins. This is without effect on the determination of the desired parameters. Similarly, the procedure serves to prevent the sensors becoming clogged and covered over during measurement.

Alternatively, the filter can be selected so that electrolytic proteins are allowed to pass while substances capable of clotting are retained.

In a third form of the invention it is possible then to even use a filter which substantially retains all the substances active in clotting, while the other components with a lower molecular weight are allowed to pass. For this purpose it is an advantage to use a filter with an exclusion limit of approximately 100,000 atomic units of mass. Using such a filter retaining the substances capable of clotting, the formation of a concentration differential for ions and the addition of heparin may be substantially avoided. Finally, the filter can be selected to allow the passage of generally all proteins and substances capable of clotting, while retaining erythrocytes.

As has already been noted supra the method in accordance with the invention is normally carried out using entire blood, which is taken from the extracorporeal circuit of the patient. In this respect it is insignificant for the invention how the blood is taken from, and is returned to the patient: it is possible to use a single or a two needle technique.

In order to obtain quantitative results it is necessary in accordance wth the invention for the space between the membrane of the filter and the analyzer, that is to say the second chamber and the plasma duct, to be shut off from the atmosphere in order to preclude access of air to the plasma obtained. Owing to the small cross section of the duct retrodiffision of the air into the open end of the duct does not play any significant role, more especially seeing that the speed of transport of the plasma is large in relation to the exchange of gases at the liquid surface.

Similarly it is insignificant for the invention what purpose the extracorporeal circuit serves. In this respect all possible purposes of the extracorporeal circuit are conceivable, as for example the establishment of such circuit for the use of a heart-lung machine, for extracorporeal membrane oxygenation, hemodialysis, plamsapheresis or plasma filtration.

It is moreover possible for the membrane filter used for performing the method to be placed upstream and-/or downstream from these means in order to determine the given parameters upstream and/or downstream from these arrangements. To this extent it is thus possible to use at least one membrane filter for the determination of the blood gas data.

The determination of the blood gas data may be undertaken using a sensor responding to the specific blood gas level. Accordingly a sensor responding to the partial oxygen pressure may be used for determining the oxygen level. In the same way for determining carbon dioxide a sensor responding to the partial pressure of the carbon dioxide will be utilized. Normally sensors will be used for this purpose which are arranged in a continuous flow system so that the sample to be examined is passed through the continuous flow duct thereof in accordance with a selected program and so that the sensors may respond to it.

Such sensors are known for the determination of the blood gas parameters and may accordingly also be used for determination of the blood gas parameters of plasma.

It is an advantage is such an analyzer in addition includes a sensor for pH values with which the pH value of the plasma may be measured, this being a useful feature for determining the acid-base equilibrium along with the two other parameters, more especially the carbon dioxide content of the blood.

In a further embodiment of the invention there is measuring device, in addition to the above-noted blood gas analyzer, for determining the electrolytes contained in the blood. It is an advantage in this respect if a continuous flow apparatus is used as described for example in the unexamined German specification No. 3,416,956 or the German Patent No. 3,524,824, the content of which is included by reference herein and made part of the present disclosure.

Further details, features and advantages of the invention will be seen from the following detailed account referring to the drawings.

DETAILED ACCOUNT OF WORKING EXAMPLES OF THE INVENTION

Figure 1:
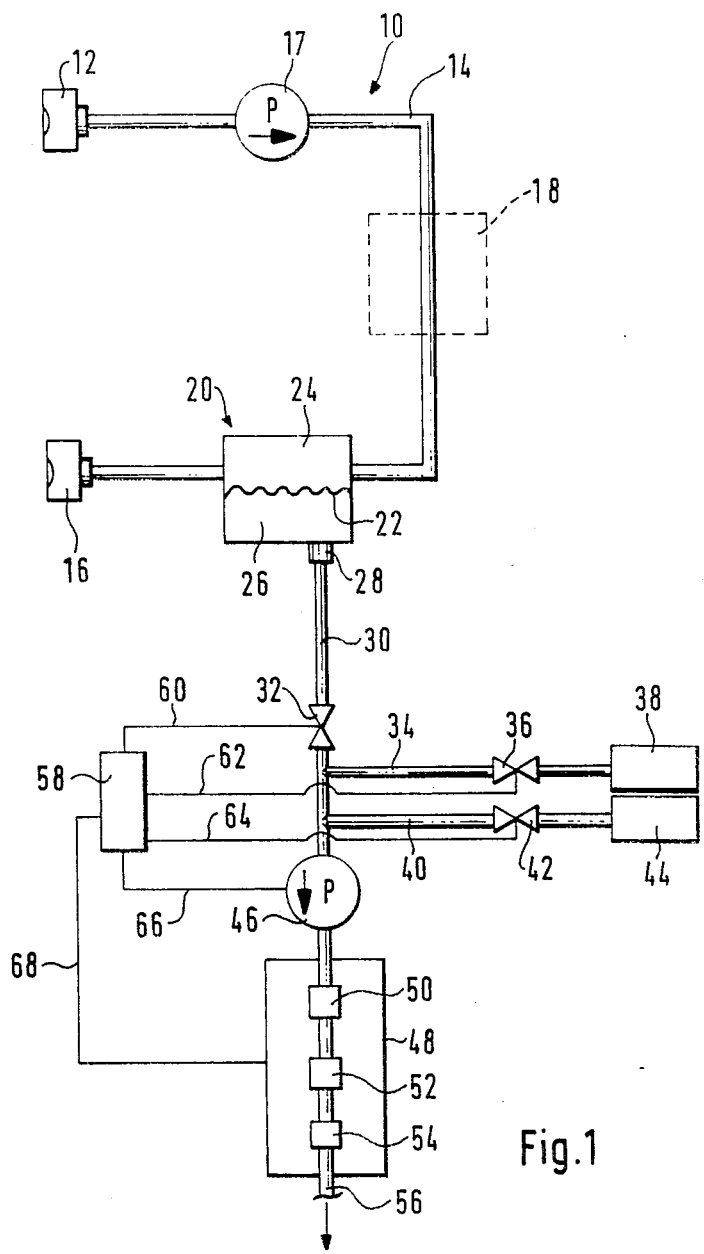
FIG. 1 is a diagrammatic view of a first form of the apparatus of the invention for determining blood gas parameters.

FIG. 1 shows a blood gas measuring device 10, which is made up of a first blood connection 12, an extracorporeal circuit 14 extending from the blood connection 12 and a second blood connection 16. Such extracorporeal circuits are familiar to those in the art and are normally produced using needles as blood tapping points or connections 12 and 16 and which are connected with the array of flexible piping forming the circuit 14. In such an extracorporeal circuit 14 it is possible to include a blood treating device 18, which is marked in broken lines in FIG. 1. Such a blood treating device 18 may for example be a heart-lung machine, a membrane oxygenator, a hemodialyzer, a plasmapheresis system or another blood treating apparatus.

The extracorporeal circuit 14 furthermore includes a membrane filter 20, which has a membrane 22, which divides the membrane filter into a first chamber 24 through which blood flows and a second chamber 26 with plasma flowing through it. In this respect the membrane 22 has the above mentioned separating properties, that is to say the separation limit of the membrane filter 20, will be selected in accordance with the particular application. The first chamber 24 is thus connected with the circuit 14, whereas the second chamber 26 has an outlet 28 from which a first plasma duct 30 extends.

In the embodiment of the invention to be seen in FIG. 1 a first valve 32 is mounted in this plasma duct. The function of the valve will be described later.

Downstream from the valve 32 the plasma duct 30 is connected with a first calibration solution duct 34 in which there is a second valve 36 and which is connected with a first calibration solution container 38.

At a point further downstream a second calibration solution duct 40 opens into the plasma duct 30. A third valve 42 is mounted in this duct 40, which is connected with a second calibration solution container 44.

Downstream from the calibration solution ducts 34 and 40 a pump 46 is arranged in the plasma duct in order to pump the plasma and, respectively, the calibration solutions, through the plasma duct 30.

The end of the plasma duct 30 opens into a blood gas analyzer 48, which as indicated in FIG. 1 is in the form of a continuous flow means in this version of the invention.

This blood gas analyzer 48 has a PO$_2$ sensitive sensor 50, and PCO$_2$ sensitive sensor 52 and preferably a pH sensitive sensor 54.

After they have flowed through this blood gas analyzer 48, the solutions are passed to the drain 56.

Furthermore for determination of the blood gas parameters the device of the invention has a control unit 58 which is connected via a first control line 60 with the valve 32, via a second control line 62 with the valve 36, via a third control line 64 with the valve 42 and via a further control line 66 with the pump 46.

The control unit 58 operates the valves and the pump in accordance with a given program so that plasma and calibration solutions are supplied to the blood gas analyzer 48 in the desired manner.

THE MANNER OF OPERATION OF THE FIRST EMBODIMENT OF THE INVENTION

In the operation of the device shown in FIG. 1 blood circulates in the extracorporeal circuit 14 and is pumped continuously by a pump 17 through the first chamber 24 of the membrane filter 20. In order to sample plasma from the membrane filter 20, after opening the valve 32, the pump 46 pumps plasma from the second chamber 26 and supplies it to the blood gas analyzer 48, in which the blood data, that is to say the oxygen and carbon dioxide partial pressures and the pH value are continuously determined.

When this measuring operation is in progress the calibration solution ducts 34 and 40 are shut off by the valves 36 and 42.

In accordance with the selected program the sensors 50 through 54 are calibrated at given intervals in time in order to preclude errors in the determination of the blood data. For this purpose the valve 32 is shut and the valves 36 and 42 are opened in sequence to cause a first and a second calibration liquid to pass through the blood gas analyzer under the action of the pump 46.

The first and second calibration solutions have different concentrations of oxygen and carbon dioxide and, if relevant, a different pH value in order to perform the calibration at different measuring points, this providing information as regards the slopes of the characteristics of the sensors. In this respect the control unit 58 sends a corresponding signal via a fifth control line 68, which is connected with the blood gas analyzer 48, whereupon the blood analyzer 48 switches over from the measuring phase to the calibration phase. This calibration phase also takes place in accordance with a selected program in the blood analyzer 48 and may be of a known type.

After the calibration the control unit 58 switches back to the measuring phase, the valve 32 being opened and the calibration solution valves 36 and 42 being shut. The next step is the renewed pumping of plasma through the plasma duct 30 to the blood gas analyzer 48.

An important feature in the performance of the novel method is that the plasma be supplied as rapidly as possible to the blood gas analyzer after tapping from the membrane. This is to preclude any chance of the gas concentration changing in the plasma as this would lead to a falsification of the blood gas data.

In this respect it is an advantage if only small amounts of plasma are taken from a suitably dimensioned membrane filter 20. For this purpose flexible piping with a small diameter is used as the plasma duct 30 and the pump 46 is in the form of a peristaltic pump without any piston or the like making direct contact with the plasma.

During the performance of the novel method it is possible to obtain blood gas data at the blood gas analyzer 48 conforming to the true values obtained using conventional techniques involving the direct sampling of entire blood which is then immediately examined in the blood gas analyzer. In this respect it is possible with the novel method and the apparatus for performing it to automatically determine the desired blood gas parameters continuously in an extracorporeal blood circuit shut off and thus kept under sterile conditions. Such direct determination in the extracorporeal circuit was previously not possible because of problems with sterility.

DESCRIPTION OF SECOND EMBODIMENT OF THE INVENTION

Figure 2:
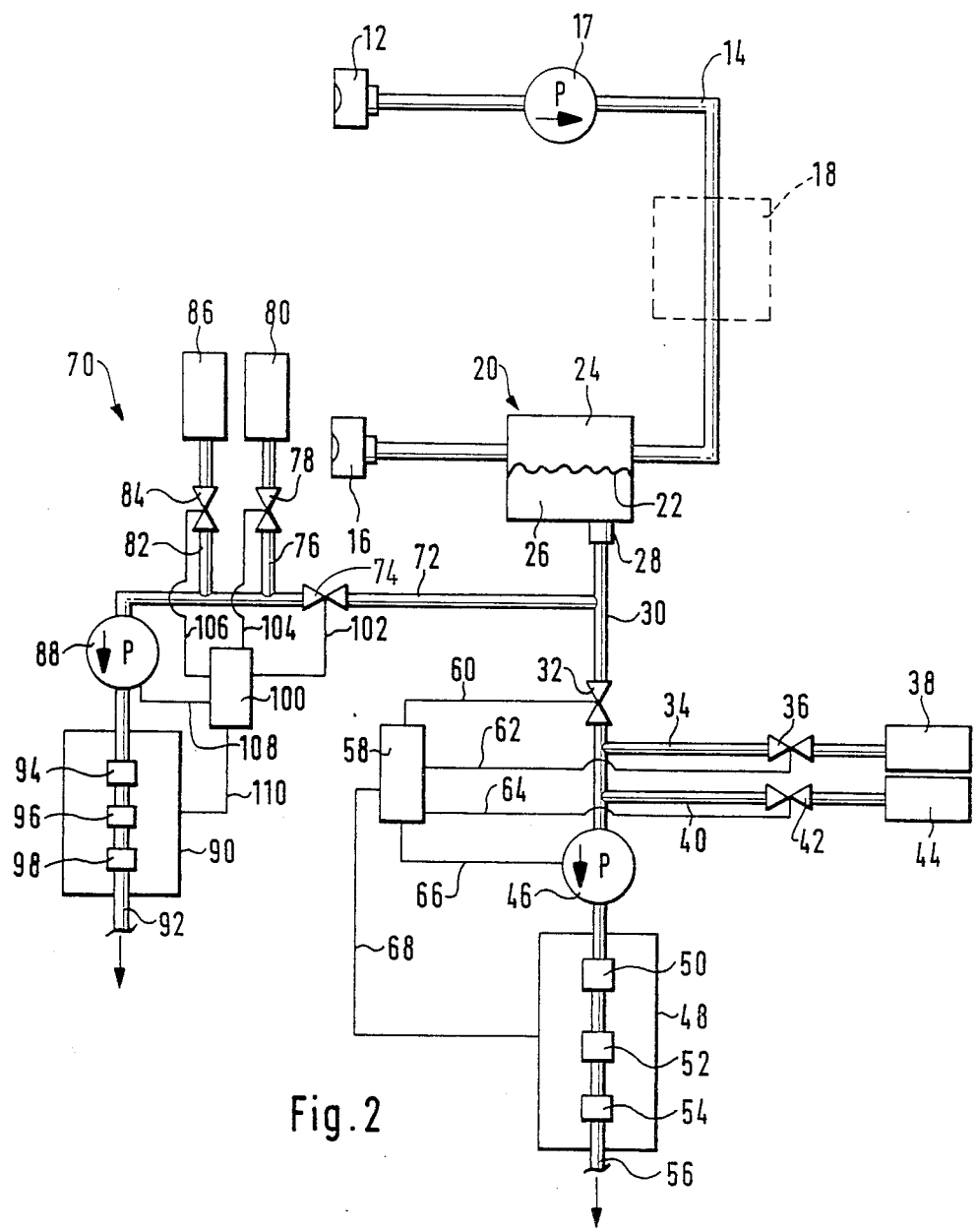
FIG. 2 is a further diagrammatic view of a second embodiment of the apparatus of the invention for determining the blood gas parameters and the ion concentration in the blood.

The second form of the novel apparatus for determining blood gas data shown in FIG. 2 is referenced 70 and in part is based on the embodiment of FIG. 1. Where there are similarities, like parts are denoted by like reference numerals.

As the reader will see from FIG. 2, a branch duct 72 extends from the plasma duct 30 between the membrane filter 20 and the first valve 32. There is a fourth valve 74 in this duct 72. Downstream from the valve 74 there branches a third calibration duct 76 with a fifth valve 78 placed therein. The end of the third calibration duct 76 is connected with a third calibration solution container 80.

Furthermore, the branch duct 72 is connected with a fourth calibration solution duct 82, in which there is a sixth valve 84 and which as its end is joined with a fourth calibration solution container 86.

Downstream from these branch ducts 76 and 82 there is a second pump 88 which is arranged in the branch duct 72 and which functionally is identical to the pump 46. Lastly the end of the branch duct 72 is connected with a device 90 for determining the ion concentration or the conductivity which in this form of the invention is shown in the form of a continuous flow means and which has an exit or drain 92 at its downstream end. As an example, this continuous flow means has an Na sensor 94, a K sensor 96 and a conductivity measuring cell 98.

Such a device 90 is for instance described in the German unexamined specification No. 3,416,956, whose content is incorporated herein by reference.

Furthermore there is an additional control unit 100 for the operation of the valves 74, 78 and 84, of the pump 88 and of the ion measuring device 90. The unit has suitable control lines 102, 104, 106, 108 and 110.

The second control unit 100 is operated in a manner similar to the first control unit 58 so that one may refer to the previous account in this respect. Therefore, in this respect for measuring the ion concentration or the conductivity of the plasma the valve 74 is opened and the pump 88 is operated. The plasma is pumped through the plasma duct 30 and the branch duct 72 to the ion measuring device 90 in which the respective ion parameters are determined. In this respect the measurement of the parameters is not limited to the above noted Na and K parameters: it is quite possible to determine other parameters such as Ca, conductivity and the like.

Following a selected program the ion measuring device 90 is calibrated at given time intervals. For this purpose the valve 74 is shut and the valve 78 and 84 are opened, the pump 88 then being used to consecutively convey two calibration solutions of different composition through the ion measuring device 90. These ion calibration solutions have certain ion concentrations in accordance with the type of sensors used and which have to be used for the calibration of the sensors and the ion measuring device 90 respectively. After calibration and setting of the null point of the ion measuring device 90 the control unit 100 switches back to the measuring phase, closing the valves 78 and 84 and then opening the valve 74 again. Following this plasma fluid to be examined may be repumped through the ion measuring device 90.

As already mentioned, the plasma filter 20 has to be suitably selected for the measurement of ions. The plasma filter must let through such proteins as bind ions lest the result of measurement be falsified by the retention of such proteins.

Therefore a membrane filter is to be employed which has an exclusion limit of at least about 100,000 atomic mass units.

As indicated in the above description the ion measuring device 90 may be preferably used as an advantageous form of the blood gas measuring device 10 with the blood gas measuring device 10. However it may also be employed by itself if this should be an advantage. It may also be combined in a single measuring instrument and in single continuous flow means, that is to say, the two measuring devices 48 and 90 would then be combined and all the other parts having an identical function, as for example the pumps 46 and 88 and the calibration arrangements would be put together. In this case it would be for example possible to use two calibration solutions in which the Na and K contents, the pH value and the partial pressures of oxygen and carbon dioxide would be at two different values in the different respective solutions.

I claim:

1. A method for determining the partial pressure of at least one gas in blood flowing in an extracorporeal circuit, comprising the steps of separating plasma containing a gas from the blood at a membrane filter, and bringing the plasma containing the gas into contact with at least one sensor responsive to the partial pressure of the gas, air being continuously excluded from the plasma and the partial pressure of the gas then being measured in the plasma during the exclusion of air.

2. An apparatus for determining the partial pressure of at least one gas in blood comprising:
    a liquid filter having a chamber space,
    a semipermeable membrane having an exclusion limit of at least 40,000 atomic mass units but not greater than an exclusion limit wherein the membrane is capable of separating plasma from blood, said membrane dividing the chamber space into first and second chambers,
    means defining an extracorporeal blood circuit connected with the first chamber,
    at least one sensor for determining the partial pressure of a gas, a first liquid duct connecting the at least one sensor with the second chamber of the filter, the second chamber having a single outlet connected with the first liquid duct, and
    a unit, placed in the first liquid duct, for conveying liquid derived from blood through the membrane of the filter.

3. The apparatus as claimed in claim 2 wherein the unit for conveying liquid is in the form of a first pump.

4. The apparatus as claimed in claim 3, further comprising:
    a first valve in the first liquid duct upstream from the first pump,
    a first calibration solution duct opening into the first liquid duct between the first pump and the first valve,
    a second valve in the first calibration solution duct, and
    a first calibration solution container joined with an end of the first calibration solution duct.

5. The apparatus as claimed in claim 4 further comprising a first control unit with control lines for connecting the first control unit with the first valve in the first liquid duct for selectively opening and closing the first valve therein and for opening and closing the second valve provided in the first calibration solution duct and operating the first pump for switching the apparatus in a measuring and in a calibration phase.

6. The apparatus as claimed in claim 5 further comprising a branch duct extending from the first liquid duct, and an ion measuring device connected with the branch duct.

7. The apparatus as claimed in claim 6, further comprising a second pump, located in the branch duct.

8. The apparatus as claimed in claim 7, further comprising:
    a third valve arranged in the branch duct upstream from the second pump,
    a second calibration solution duct opening into the branch duct between the third valve and the second pump,
    a fourth valve in the second calibration solution duct, and
    a second calibration solution container arranged at an end of the second calibration solution duct.

9. The apparatus as claimed in claim 8, further comprising a second control unit with control lines for operation of the third valve in the branch duct, the fourth valve in the second calibration solution duct and the ion measuring device in accordance with a program.

10. The apparatus as claimed in claim 2, wherein the at least one sensor comprises a plurality of sensors contained in a blood gas analyzer and wherein the plurality of sensors includes a $PO_2$ sensor and a $PCO_2$ sensor.

11. The apparatus as claimed in claim 10, further comprising a pH sensor in the analyzer.

12. The apparatus as claimed in claim 2 wherein the semipermeable membrane is a hemofilter with an exclusion limit of 40,000 to 60,000 atomic mass units.

13. The apparatus as claimed in claim 2 wherein the semipermeable membrane has such an exclusion limit that electrolytic proteins are allowed to pass while substances capable of clotting are retained.

14. The apparatus as claimed in claim 13 wherein the semipermeable membrane has an exclusion limit of approximately 100,000 atomic mass units.

15. The apparatus as claimed in claim 2 wherein the semipermeable membrane is such that it allows the passage of generally all proteins and substances capable of clotting while retaining erythrocytes.

* * * * *